US009228943B2

(12) United States Patent
Wang et al.

(10) Patent No.: US 9,228,943 B2
(45) Date of Patent: Jan. 5, 2016

(54) DYNAMICALLY ADJUSTABLE SEMICONDUCTOR METROLOGY SYSTEM

(71) Applicant: KLA-Tencor Corporation, Milpitas, CA (US)

(72) Inventors: David Y. Wang, Santa Clara, CA (US); Guorong Vera Zhuang, Santa Clara, CA (US); Johannes D. de Veer, Menlo Park, CA (US); Kevin Peterlinz, Fremont, CA (US); Shankar Krishnan, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 302 days.

(21) Appl. No.: 13/661,752

(22) Filed: Oct. 26, 2012

(65) Prior Publication Data
US 2013/0114085 A1 May 9, 2013

Related U.S. Application Data

(60) Provisional application No. 61/552,104, filed on Oct. 27, 2011.

(51) Int. Cl.
*G01B 11/14* (2006.01)
*G01N 21/55* (2014.01)
*G01N 21/21* (2006.01)

(52) U.S. Cl.
CPC ............. *G01N 21/55* (2013.01); *G01N 21/211* (2013.01); *G01N 2021/213* (2013.01); *G01N 2021/556* (2013.01)

(58) Field of Classification Search
CPC ............... G01N 2021/213; G01N 2021/556; G01N 21/211; G01N 21/55
See application file for complete search history.

(56) References Cited

U.S. PATENT DOCUMENTS

| | | | |
|---|---|---|---|
| 5,859,424 A | 1/1999 | Norton et al. | |
| 6,844,927 B2* | 1/2005 | Stokowski et al. | ........ 356/237.1 |
| 7,076,321 B2 | 7/2006 | Purdy | |
| 7,619,735 B2 | 11/2009 | Milshtein | |
| 2011/0069312 A1* | 3/2011 | Kandel et al. | .................. 356/369 |
| 2012/0196271 A1* | 8/2012 | Ingber | .............................. 435/3 |
| 2012/0224183 A1* | 9/2012 | Fay et al. | ....................... 356/491 |
| 2012/0327503 A1* | 12/2012 | Manassen et al. | ............. 359/291 |
| 2013/0304408 A1* | 11/2013 | Pandev | ........................... 702/83 |

* cited by examiner

*Primary Examiner* — Gregory J Toatley
*Assistant Examiner* — Shawn Decenzo
(74) *Attorney, Agent, or Firm* — Suiter Swantz pc llo

(57) ABSTRACT

The present invention may include an illumination source, a detector, a selectably adjustable optical system including a dynamically adjustable illumination pupil of the illumination arm, a dynamically adjustable collection pupil of the collection arm, a dynamically adjustable illumination field stop of the illumination arm, a dynamically adjustable collection field stop of the collection arm, a sensor configured to measure one or more optical characteristics of one or more components of the optical system, and a control system configured to selectably dynamically adjust at least one of the illumination pupil, the collection pupil, the illumination field stop, the collection field stop, and a spectral radiance of the illumination source.

41 Claims, 11 Drawing Sheets

DYNAMICALLY ADJUSTABLE SEMICONDUCTOR METROLOGY SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled METHODS AND APPARATUS FOR DYNAMICALLY OPTIMIZING SEMICONDUCTOR METROLOGY SYSTEM PERFORMANCE, naming David Y. Wang, Guorong Vera Zhuang, Johannes D. de Veer, Kevin Peterlinz, and Shankar Krishnan as inventors, filed Oct. 27, 2011, Application Ser. No. 61/552,104.

TECHNICAL FIELD

The present invention generally relates to a method and system for dynamically adjusting performance of a semiconductor metrology tool, and, in particular, a method and system for improving accuracy, precision, sensitivity, sample/target measurement spot size and throughput of a metrology tool using dynamic adjustments of components of the metrology tool.

BACKGROUND

As demand for ever-shrinking semiconductor devices continues to increase, so too will the demand for improved semiconductor wafer metrology systems. The fabrication of semiconductor devices, such as logic and memory devices, typically includes processing a semiconductor wafer using a large number of semiconductor fabrication processes to form various features and multiple levels of the semiconductor devices. Multiple semiconductor devices may be fabricated in an arrangement on a single semiconductor wafer and then separated into individual semiconductor devices.

Metrology processes are used at various steps during a semiconductor manufacturing process to monitor and control one or more semiconductor layer processes. For example, metrology processes are used to measure one or more characteristics of a wafer such as dimension (e.g., line width, pitch, feature shape. thickness, etc.) of features formed on the wafer during a process step, wherein the quality of the process step can be determined by measuring the one or more characteristic parameters deemed to be critical. In this scenario, a given semiconductor sample may include a set of metrology targets, with film stacks or two-dimensional and three-dimensional patterned structures surrounded by one or more materials of various geometries and properties.

In a diffraction limited system, the spatial resolution of the given metrology tool is provided by the Rayleigh criterion, namely:

$$d = \frac{1.22\lambda}{NA} \qquad \text{Eq. 1}$$

where $\lambda$ represents the wavelength of the illumination used by the optical system of the metrology tool and NA is the numerical aperture of the optical system of the metrology tool. In the case of ellipsometry-, polarized and unpolarized reflectometry-, and scatterometry-based metrology measurements, quantitative results (e.g., film thickness, critical dimension (CD), and the detailed feature shape) are generally impacted significantly by diffraction. As such, it would be advantageous to provide a metrology system that aids in mitigating the fidelity loss on the measurements as a result of diffraction effects.

SUMMARY

A dynamically adjustable metrology system is disclosed. In one aspect, the system may include, but is not limited to, an illumination source configured to illuminate one or more metrology targets disposed on a surface of a sample disposed on a sample stage; a detector configured to detect at least a portion of light reflected from the one or more metrology targets; a selectably adjustable optical system including an illumination arm and a collection arm, the illumination source and the detector being optically coupled by the optical system, the optical system further including at least one of the group including: a dynamically adjustable illumination pupil positioned in the illumination arm, a dynamically adjustable collection pupil positioned in the collection arm, a dynamically adjustable illumination field stop positioned in the illumination arm, a dynamically adjustable collection field stop positioned in the collection arm; a sensor configured to measure one or more optical characteristics of at least one of the dynamically adjustable illumination pupil, the dynamically adjustable collection pupil, the dynamically adjustable illumination field stop, the dynamically adjustable collection field stop and the one or more metrology targets of the sample; a control system communicatively coupled to at least one of the dynamically adjustable illumination pupil, the dynamically adjustable collection pupil, the dynamically adjustable illumination field stop and the dynamically adjustable collection field stop, wherein the control system is configured to: receive one or more optical characteristics of at least one of the dynamically adjustable illumination pupil, the dynamically adjustable collection pupil, the dynamically adjustable illumination field stop, the dynamically adjustable collection field stop and the one or more metrology targets of the sample from the sensor; monitor one or more optical characteristics of one or more metrology targets of the sample; responsive to the measured one or more optical characteristics, selectably dynamically adjust at least one of the illumination pupil, the collection pupil, the illumination field stop, the collection field stop, and a spectral radiance of the illumination source. In a further aspect, the control system is configured to dynamically selectably adjust at least one of the illumination pupil and the collection pupil in order to control at least one of a numerical aperture (NA), an angle of incidence (AOI), range of azimuth angles (AZ), section of azimuthal angles and pupil apodization of the metrology system. In a further aspect, the control system is configured to dynamically selectably adjust the illumination field stop and the collection field stop in order to control a field of view (FOV) of the metrology system. In a further aspect, the control system is configured to dynamically selectably adjust the spectral radiance of the illumination source in order to reduce signal contamination below a selected tolerance level. In a further aspect, signal contamination can be reduced by programming the spectral detection range of the detector. In addition, the spectral detection region of the detector may be selected and programmed to reduce signal contamination by eliminating the longer wavelength illumination having higher diffraction contamination and less target information.

A dynamically adjustable metrology system is disclosed. In one aspect, the system may include, but is not limited to, an illumination source configured to illuminate one or more metrology targets disposed on a surface of a sample disposed on a sample stage; a spectrograph configured to measure spectral properties of at least a portion of light reflected from the one or more metrology targets; a selectably adjustable optical system including an illumination arm and a collection arm, the illumination source and the detector being optically coupled by the optical system, the optical system further including at least one of the group including: a dynamically adjustable illumination pupil positioned in the illumination arm, a first polarizing element positioned in the illumination arm, a dynamically adjustable illumination field stop positioned in the illumination arm, a dynamically adjustable collection pupil positioned in the collection arm, a second polarizing element disposed in the collection arm, and a dynamically adjustable collection field stop positioned in the collection arm; a sensor configured to measure one or more optical characteristics of at least one of the dynamically adjustable illumination pupil, the dynamically adjustable collection pupil, the dynamically adjustable illumination field stop the dynamically adjustable collection field stop and one or more metrology targets of the sample; a control system communicatively coupled to the dynamically adjustable illumination pupil, the dynamically adjustable collection pupil, the dynamically adjustable illumination field stop and the dynamically adjustable collection field stop, wherein the control system is configured to: receive one or more optical characteristics of at least one of the dynamically adjustable illumination pupil, the dynamically adjustable collection pupil, the dynamically adjustable illumination field stop and the dynamically adjustable collection field stop from the sensor; monitor one or more optical characteristics at one or more metrology targets of the sample; responsive to the measured one or more optical characteristics, selectably dynamically adjust at least one of the illumination pupil, the collection pupil, the illumination field stop, the collection field stop, spectral range detection range of the detector and a spectral radiance of the illumination source. In a further aspect, the control system is configured to dynamically selectably adjust at least one of the illumination pupil and the collection pupil in order to control at least one of a numerical aperture (NA), an angle of incidence (AOI), range of azimuth angles (AZ) and pupil apodization of the metrology system. In a further aspect, the control system is configured to dynamically selectably adjust the illumination field stop and the collection field stop in order to control a field of view (FOV) of the metrology system. In a further aspect, the control system is configured to dynamically selectably adjust the spectral radiance of the illumination source in order to reduce signal contamination below a selected tolerance level. In addition, the spectral detection region of the detector may be selected and programmed to reduce signal contamination by eliminating the longer wavelength illumination having higher diffraction contamination and less target information.

A dynamically adjustable metrology system is disclosed. In one aspect, the dynamically adjustable metrology system may include, but is not limited to, an illumination source configured to illuminate one or more metrology targets disposed on a surface of a sample disposed on a sample stage; a detector configured to detect at least a portion of light reflected from the one or more metrology targets; a selectably adjustable optical system including an illumination arm and a collection arm, the illumination source and the detector being optically coupled by the optical system, the optical system further including at least one of the group including: an illumination pupil positioned in the illumination arm; a collection pupil positioned in the collection arm; an illumination field stop positioned in the illumination arm; and a collection field stop positioned in the collection arm, wherein at least one of the illumination pupil, the collection pupil, the illumination field stop and the collection field stop is dynamically adjustable, wherein at least one of the illumination pupil, the collection pupil, the illumination field stop and the collection field stop is static; a sensor configured to measure one or more optical characteristics of at least one of the illumination pupil, the collection pupil, the illumination field stop, the collection field stop and the one or more metrology targets of the sample; a control system communicatively coupled to at least one of the illumination pupil, the collection pupil, the illumination field stop and the collection field stop, wherein the control system is configured to: receive one or more optical characteristics of at least one of the illumination pupil, the collection pupil, the illumination field stop, the collection field stop and the one or more metrology targets of the sample from the sensor; monitor one or more optical characteristics of one or more metrology targets of the sample; responsive to the measured one or more optical characteristics, selectably dynamically adjust at least one of the illumination pupil, the collection pupil, the illumination field stop, the collection field stop, and a spectral radiance of the illumination source.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1A:
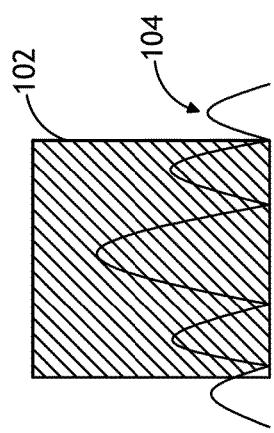
FIGS. 1A-1C illustrate a series of conceptual views of point spread functions at the sample plane of a metrology target, in accordance with one embodiment of the present invention.

Reference will now be made in detail to the subject matter disclosed, which is illustrated in the accompanying drawings.

Referring generally to FIGS. 1A through 8, a dynamically adjustable metrology system 200 is described in accordance with the present disclosure. The present disclosure is directed toward a dynamically adjustable metrology tool 200 system suitable for enhancing metrology measurement performance, as quantified by metrics, such as but not limited to, accuracy, precision, matching, sensitivity, AOI, AZ range and the like. The metrology system 200 includes several operation modes, as discussed throughout the present disclosure, which may be used independently or in combination in order to improve the measurement performance of the metrology system 200. Since the metrology system 200 of the present disclosure carries out metrology measurements over a finite target area, various optical materials surrounding a measured metrology target may contribute to the illumination of the metrology system, as a result of diffraction, and act to contaminate the scattered or reflected signal from the measured target. This contamination is undesirable and it is therefore desirable to eliminate or at least mitigate its presence. By reducing the impact of contamination, the measurement target size may be reduced for a given metrology system, while also maintaining the quality of the metrology measurements (e.g., precision, accuracy, throughput, and the like).

Responsive to one or more characteristics (e.g., point spread function, sample target measurement spot size, scattering characteristics and the like) of an analyzed metrology target of a sample (e.g., semiconductor wafer 206), the dynamically adjustable metrology tool 200 of the present invention is configured to adjust aperture and reflectivity profiles of the optical system of the metrology tool 200 in order to control the first order properties of the optical metrology system 200 including, but not limited to, angle of incidence (AOI), azimuth angle (AZ) selection and range, numerical aperture (NA), field of view (FOV), and apodization of the tool 200. In addition, the dynamically adjustable metrology tool 200 of the present invention may also be configured to dynamically adjust the spectral radiance of illumination, and spectral detection range of the detector (e.g., illumination of illumination path 212 or illumination of collection path 214) of the metrology tool 200. The control of these properties allows for the control of various measurement characteristics of the system 200 including, but not limited to, the point spread function (PSF), the spot size and one or more scattering characteristics of the illumination at the sample plane of the sample 206. Moreover, a tailored PSF through properly designed apodization function at illumination pupil plane for a measured metrology target allows for the elimination or at least a reduction of the contamination resulting from the material surrounding the analyzed metrology target of the sample. Applicant notes that the present invention may be implemented in various optical metrology configurations, such as, but not limited to, spectroscopic ellipsometry, spectroscopic polarized and unpolarized reflectometry, and spectroscopic scatterometry.

Figure 1B:
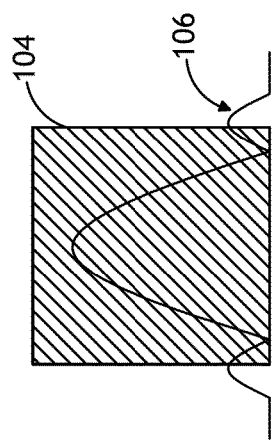
Figure 1C:
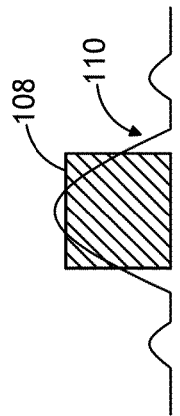

FIG. 1A illustrates a typical point spread functions (PSFs) 104 for a diffraction limited optical system with an illumination beam directed onto the metrology target 104. Point spread function depicts a large central lobe (0th order) along with multiple higher-order peaks extending beyond the spatial extent of the metrology target 104. In one aspect, the present invention may be utilized in conjunction with a reference target (i.e., target having identical scaled-up structures as device structures) to characterize spectroscopic metrology system performance as a function of target size. It is further noted that the degree the PSF extends beyond a given metrology target border may be controlled using an apodization function. For example, by implementing an apodization function at the illumination pupil plane, wherein the apodization function is specifically designed for a particular target size, the higher orders of the PSF falling outside of the target may be greatly suppressed. For instance, the SPF in FIG. 1A does not have a properly designed apodization function, while the SPF in FIG. 1B has a designed apodization function suitable for suppressing high order diffraction lobes from extending beyond the target boundaries. This characterization may be carried out by comparing measurement results over progressively smaller target sizes (see FIGS. 1D and 1E discussed further herein). As shown in FIG. 1B, an apodizer (not shown) may be implemented in a spectroscopic ellipsometry setting and other normal incidence or oblique incidence spectroscopic polarized and unpolarized reflectometry settings to obtain the desired point spread function 106 at a given metrology target 104. By modifying the illumination pupil transmittance function of the optical metrology system 200 utilizing an apodizer, the diffraction tails of the point spread function at the target 104 can be controlled and suppressed. As shown in FIG. 1C, if the higher-order diffraction tails of the point spread function 110 may be suppressed to the point wherein the point spread function core (i.e., the central lobe) is larger than the spatial extent of the given metrology target 108. The use of an apodizer to reduce diffraction tails in an optical measurement system is described generally by Norton et al. in U.S. Pat. No. 5,859,424, issued on Jan. 12, 1999, which is incorporate herein in the entirety. Applicants note that, in addition to dynamically adjusting the optical metrology systems' first order properties (e.g., AOI, AZ, NA, FOV), the present invention may control the source wavelength spectrum in order to obtain a desired point spread function at the sample plane. In addition, an "optimized" apodizer function may be implemented that is tailored to each individual analyzed sample.

Figure 1E:
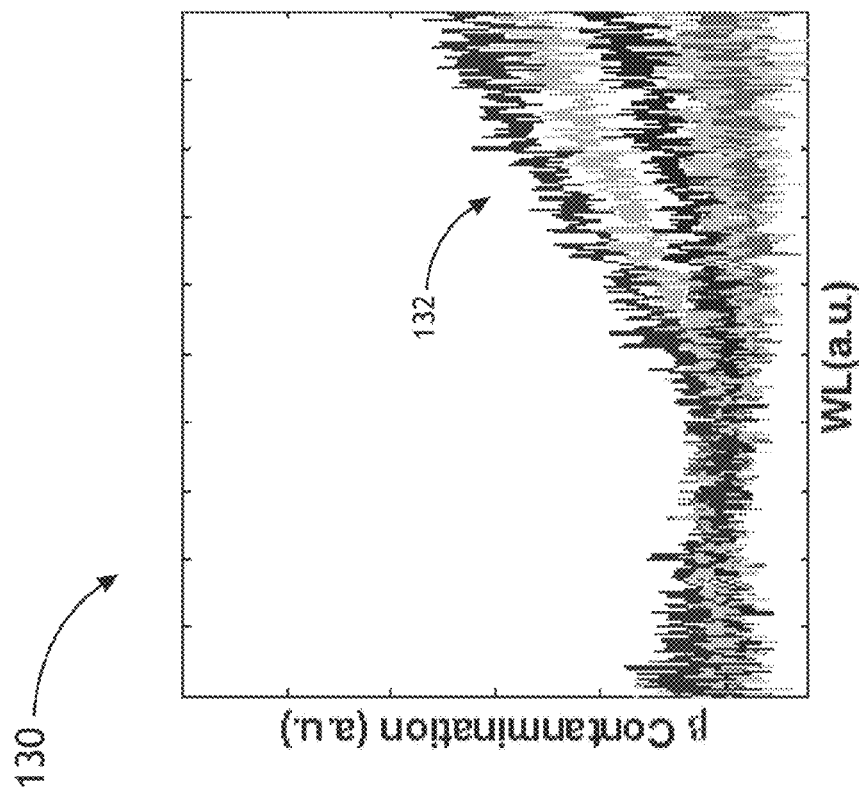
FIGS. 1D-1E illustrate signal contamination in Aa and AB as a function of wavelength for a spectroscopic ellipsometry/scatterometry system, in accordance with one embodiment of the present invention.
Figure 1D:
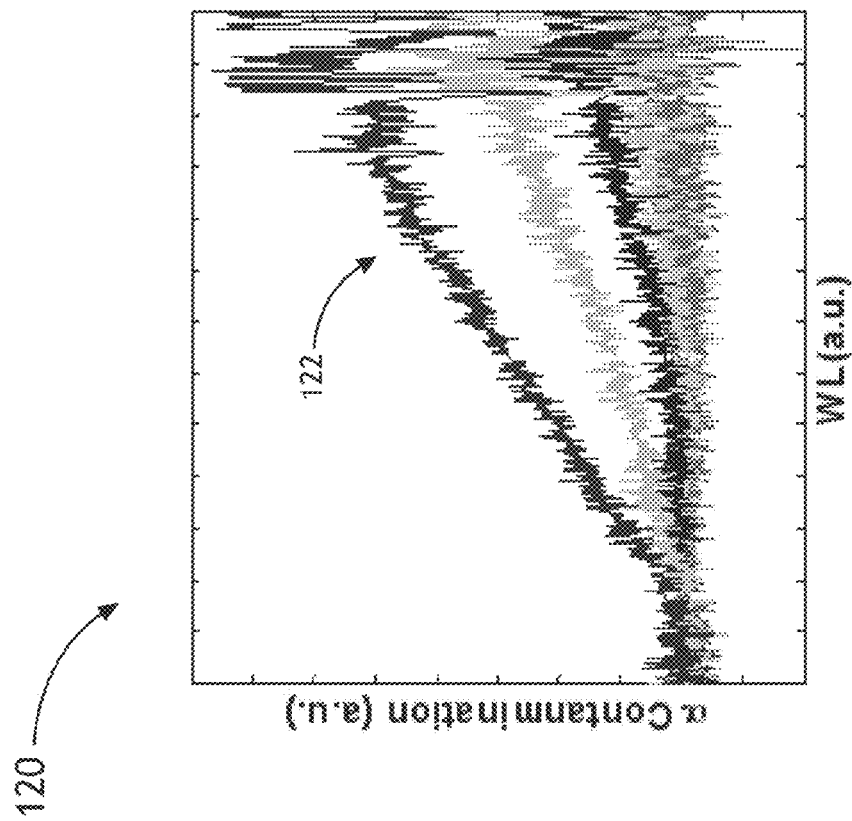

FIGS. 1D and 1E illustrate a series of signal contamination curves as a function of wavelength for various targets on a selected sample, in accordance with an embodiment of the present invention. The series of signal contamination curves may be presented in terms of the spectroscopic ellipsometry parameters, Aa and AB, a shown in graph 120 of FIG. 1D and graph 130 of FIG. 1E respectively. In the examples illustrated in FIGS. 1D and 1E the size of the target reduces for each progressively upward data set. In this sense, signal contamination for both the parameters Aa and AB generally increases as target size gets smaller and smaller. This feature is accentuated at larger wavelength. In another aspect of the present invention, the wavelength range and wavelength selection of illumination source 102 is dynamically adjustable to optimize one or more parameters detected by sensor 110. For example, the wavelength selection of illumination source 102 is dynamically adjusted to minimize the signal contamination, as that found in FIGS. 1D and 1E, for each target on sample 206.

Figure 2:
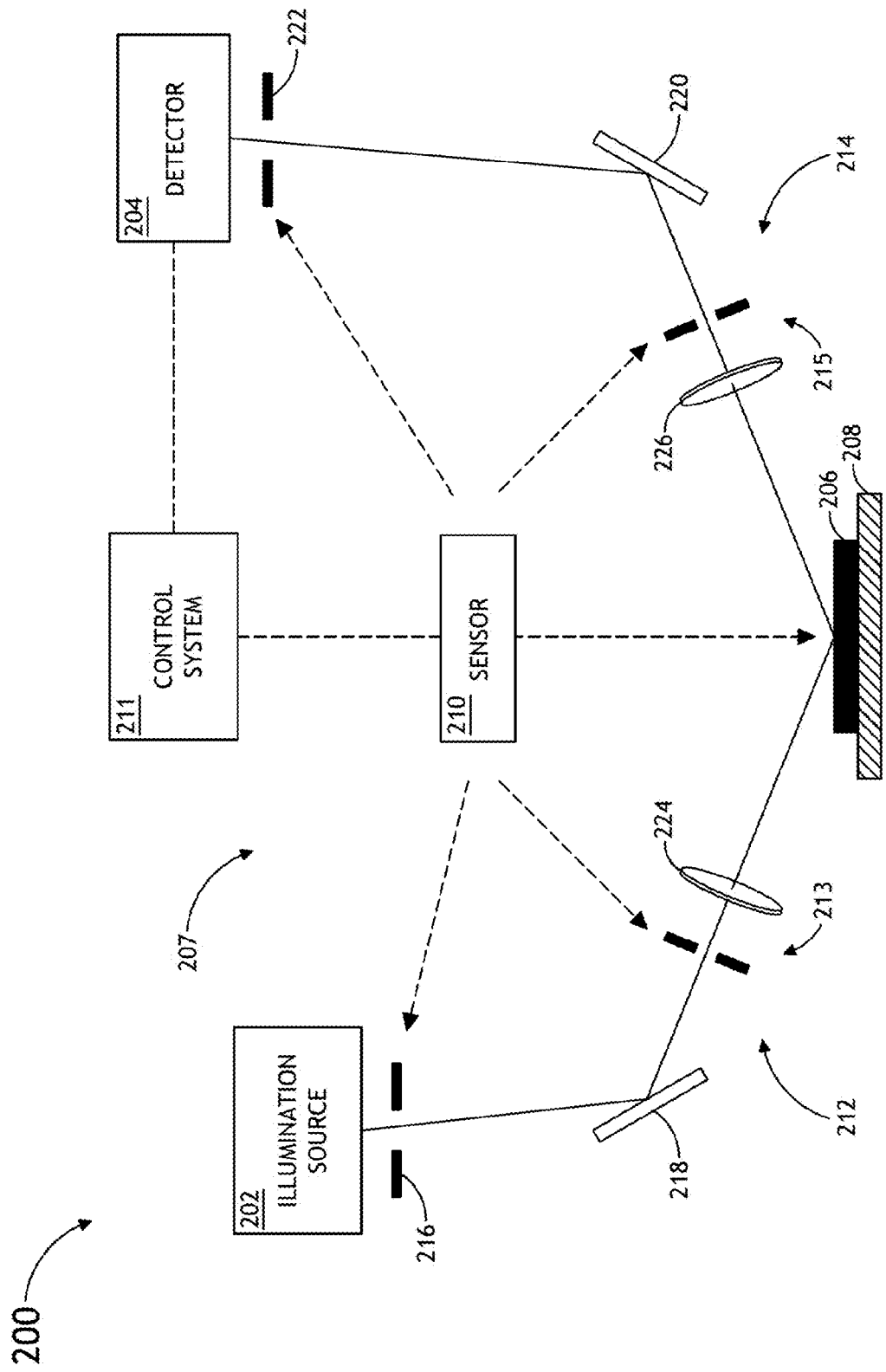
FIG. 2 illustrates a block diagram view of a dynamically adjustable metrology system, in accordance with one embodiment of the present invention.

FIG. 2 illustrates a schematic view of a dynamically adjustable metrology system 200, in accordance with one embodiment of the present invention. The system 200 may include an illumination source 202 configured to illuminate one or more metrology targets of a surface of a sample 206 disposed on a sample stage 208, a detector 204 configured to detect light reflected from the one or more metrology targets of surface of the sample 106, and a selectably adjustable optical system 207, which acts to optically couple the illumination source 202 and the detector 204. The system 200 may further include a computer control system 211 suitable for controlling the configuration of the selectably adjustable optical system 207. In addition, the system 200 may include a sensor 210 suitable for measuring one or more optical characteristics of one or more components of the system 200 and then feeding those results to the control system 211.

In one aspect of the present invention, the selectably adjustable optical system 207 of the system 200 may include an illumination arm 212 and a collection arm 214. The illumination source 202 and the detector 204 may be optically coupled via the illumination arm 212 and the collection arm 214 of the optical system 207. In this manner, light may emanate from the illumination source 202 and travel along the illumination arm 212 to the surface of the sample 206. Light reflected from one or more metrology targets disposed on the sample 206 may then travel from the surface of the sample 206 to the detector 204 along the collection arm 214.

In another aspect of the present invention, the illumination arm 212 of the optical system 207 may include a dynamically adjustable illumination field stop 216. In another aspect, the collection arm 214 of the optical system 207 may include a dynamically adjustable collection field stop 222. In a further aspect, the dynamically adjustable illumination field stop 216 and the collection field stop 222 are configured for selective control by the control system 211, allowing for dynamic adjustment of the field of view (FOV) of the metrology system 200.

In another aspect of the present invention, the illumination arm 212 of the optical system 207 may include a dynamically adjustable illumination pupil 213. In another aspect, the collection arm 214 of the optical system 207 may include a dynamically adjustable collection pupil 215. In a further aspect, the dynamically adjustable illumination pupil 213 and the collection pupil 215 are configured for selective control by the control system 211, allowing for dynamic adjustment of one or more first order parameters of the metrology system 200, such as, but not limited to, numerical aperture (NA), an angle of incidence (AOI), an azimuth angles and angle range (AZ), and apodization function. In one embodiment, the dynamically adjustable illumination pupil 213 is configured for selective control by the control system 211, allowing for dynamic adjustment of one or more first order parameters of the metrology system 200 and/or controlling signal contamination incident on one or more metrology targets on the sample 206. In another embodiment, the dynamically adjustable collection pupil 215 is configured for selective control by the control system 211, allowing for dynamic adjustment of one or more first order parameters of the metrology system 200 and/or controlling signal contamination from the one or more metrology targets on the sample 206.

In a general sense, the ability of the control system 211 to control the dynamically adjustable illumination pupil 213, the dynamically adjustable collection pupil 215, the dynamically adjustable illumination field stop 216, and the dynamically adjustable collection field stop 222 allows for the control of one or more of the first order optical parameters of the optical system 207 of the metrology system 200. In turn the control of the first order optical properties (e.g., FOV, AOI, AZ, NA, and the like) of the system 200 allows for control of the measurement performance of the metrology system 200. It is noted that control of the first order properties of the metrology system 200 allows for the control of the PSF such that the PSF is optimized or at least established beyond a suitable tolerance level with respect to a given set of characteristics (e.g., size, shape, required throughput, required accuracy, required precision and the like) of the analyzed metrology targets. In this regard, the various dynamically adjustable components may be controlled in combination or on an individual basis to achieve an adequate PSF at the sample 206 plane.

In one embodiment, the dynamically adjustable illumination field stop 216 or the dynamically adjustable collection field stop 222 may include, but are not limited to, a one dimensional or two-dimensional liquid crystal cell spatial light modulator (SLM) situated at or near the illumination or collection field stop, wherein each SLM is configured to dynamically adjust a field of view (FOV) of the metrology system. In another embodiment, the dynamically adjustable illumination field stop 216 or the dynamically adjustable collection field stop 222 may include, but are not limited to, a MEMS situated at or near the illumination or collection stop, wherein each MEMS is configured to dynamically adjust a field of view (FOV) of the metrology system. In another embodiment, the dynamically adjustable illumination field stop 216 or the dynamically adjustable collection field stop 222 may include, but are not limited to, an adjustable iris situated at or near the illumination or collection field stop, wherein each adjustable iris is configured to dynamically adjust a field of view (FOV) of the metrology system. In another embodiment, the dynamically adjustable illumination field stop 216 or the dynamically adjustable collection field stop 222 may include, but are not limited to, a set of switchable irises of different sizes situated at or near illumination or collection field stop, wherein each set of irises is configured to dynamically adjust a field of view (FOV) of the metrology system.

In one embodiment, the dynamically adjustable illumination pupil 213 or the dynamically adjustable collection pupil 215 are configured to carry out a programmed apodization function from the control system 211. In one embodiment, the dynamically adjustable illumination pupil 213 or the dynamically adjustable collection pupil 215 may include, but are not limited to, a one-dimensional or two-dimensional liquid crystal cell spatial light modulator (SLM) situated at or near the illumination pupil or collection pupil, whereby each SLM is configured to dynamically adjust at least one of an AOI, an AZ, an AZ range, a NA, and apodization of the illumination (e.g., illumination from illumination source 202 or illumination from sample surface 206).

In another embodiment, the dynamically adjustable illumination pupil 213 or the dynamically adjustable collection pupil 215 may include, but are not limited to, a one-dimensional or two-dimensional reflective MEMS mirror situated at or near the illumination pupil or collection pupil, whereby each MEMS mirror is configured to dynamically adjust at least one of an AOI, an AZ, a NA, and apodization of the illumination (e.g., illumination from illumination source 202 or illumination from sample surface 206). In another embodiment, the illumination pupil 213 and the collection pupil 215 may include, but are not limited to, one or more transmissive MEMS devices or other transmissive optical elements. In another embodiment, the system 200 may include, but is not limited to, illumination relay optics 218 and collection relay optics 220. The illumination relay optics 218 are suitable for directing illumination from the source 202 to the entrance of illumination pupil 213, while the collection relay optics 220 are suitable for directing illumination reflected or scattered off of the sample 206 to the collection pupil 215.

In another aspect of the invention, one or more sensors 210 may measure one or more characteristics of the illumination (e.g. illumination from illumination source 202 or illumination from sample surface 106) at or near the dynamically adjustable illumination field stop 216, dynamically adjustable collection field stop 222, dynamically adjustable illumination pupil 213, dynamically adjustable collection pupil 215 and one or more metrology targets of the sample 206 of metrology system 200. In some embodiments, the sensor 210 may include, but not limited to, one or more sensors for measuring point spread function (PSF), images of selected wavelength, spot size, scattering characteristics, wavefront characteristics, AOI, AZ, FOV and NA of the illumination spot on sample 206. Applicants note that in instances where the metrology system 200 is a broadband spectroscopic system, some characteristics, such as, but not limited to, PSF, spot size, scattering characteristic, wavefront characteristics, and NA are functions of wavelength. These characteristics may be quantified at specific spectral region in which signal contamination is present. As a result of diffraction effects, signal contamination becomes more of an issue at larger and larger wavelength, as indicated by Eq. 1 above. In this sense, the longer the wavelength and the smaller the NA, the more significant the diffraction (i.e., spot size deviate more significantly from its intended geometrical spot).

In another aspect of the invention, the control system 211 may control the various optical elements of the system 200, such as the illumination stop 216, illumination pupil 213, collection stop 222, and the collection pupil 215. In one embodiment, upon receiving one or more characteristics of the dynamically adjustable illumination pupil 213, the dynamically adjustable collection pupil 215, the dynamically adjustable illumination field stop 216, the dynamically adjustable collection field stop 222 or the one or more metrology targets of the sample 206 from the sensor 210, the control system 211 may selectably adjust the dynamically adjustable illumination pupil 213 or the dynamically adjustable collection pupil 215 in order to control at least one of a numerical aperture (NA), an angle of incidence (AOI), azimuth angles (AZ), AZ angle range and pupil apodization of the metrology system 200.

In another embodiment, upon receiving one or more characteristics of the dynamically adjustable illumination pupil 213, the dynamically adjustable collection pupil 215, the dynamically adjustable illumination field stop 216, the dynamically adjustable collection field stop 222 or the one or more metrology targets of the sample 206 from the sensor 210, the control system 211 may selectably adjust the dynamically adjustable illumination field stop 216 and/or the dynamically adjustable collection field stop 22 in order to control a field of view (FOV) of the metrology system 200.

In another aspect of the present invention, the control system 211 is configured to dynamically adjust the spectral radiance of the illumination in a portion of the metrology system 200. In this regard, the control system 211 may adjust the spectral radiance of illumination (e.g., illumination of illumination path 212 or illumination in collection path 214) in order to reduce signal contamination below a selected tolerance level. It is noted that by modifying the spectral radiance of illumination of light incident on one or more metrology targets of the sample 206 the control system 211 may act to modify the PSF such that the PSF is optimized or at least established beyond a suitable tolerance level (e.g., tails of PSF extending beyond target surface are reduced or eliminated—see FIGS. 1A-1C) with respect to a given set of characteristics (e.g., size, shape, required throughput, required accuracy, required precision and the like) for the analyzed metrology targets. For example, control system 211 may adjust the spectral radiance of the illumination such that a setoff pre-determined metrology parameter specifications are achieved. Further, the control system 211 may adjust the spectral radiance of illumination in order to minimize signal contamination.

In one embodiment, the illumination source 202 of the metrology system 200 may include one or more spectra-adjustable illumination sources. In a further embodiment, the control system 211 may be communicatively coupled to the illumination source 202 and further configured to control one or more spectral characteristics (e.g., output wavelength, output wavelength range, and the like). In one embodiment, upon receiving one or more characteristics of the one or more metrology targets of the sample 206 from the sensor 210, the control system 211 may selectably adjust one or more spectral characteristics of the illumination source 202 in order to control signal contamination (e.g., light contamination from material surrounding a given target). In this regard, the control system 211 may adjust the illumination source 202 output such that the illumination emanating from the illumination source 202 has a higher spectral radiance in a spectral region having lower signal contamination.

In another aspect of the present invention, the control system 211 is configured to dynamically adjust the detection spectral range of the detector. In a further embodiment, signal contamination can be reduced by programming the spectral detection range of the detector. In addition, the spectral detection region of the detector may be selected and programmed to reduce signal contamination by eliminating the longer wavelength illumination having higher diffraction contamination and less target information.

In another embodiment, the metrology system 200 may include one or more selectable filters disposed along the optical system 207 (e.g., disposed in illumination path 212 or disposed in collection path 214) configured to attenuated spectral radiance at a wavelength range displaying a contamination level above a suitable tolerance level. For example, the selectable filter may include, but is not limited to, an apodizing filter, low pass filter and notch filter. In a further embodiment, the control system 211 may be communicatively coupled to the selectable filter and further configured to insert the filter into an optical pathway (e.g., illumination pathway 212 or collection pathway 214) of the metrology system 200, whereby the selectable filter is configured to attenuate the spectral radiance at a selected wavelength range (e.g., wavelength range displaying a contamination level above a desired tolerance level). In one embodiment, upon receiving one or more characteristics of the one or more metrology targets of the sample 206 from the sensor 210, the control system 211 may selectably actuate the filter into or out of the illumination path 212 or collection path 214 of the metrology system 200 in order to control signal contamination associated with a given target. In this regard, upon receiving an indication from the sensor 210 that contamination associated with a given metrology target is above a desired tolerance level, the control system 211 may actuate the filter into the illumination path 212 or collection path 214 of the metrology system 200 in order to attenuate spectral radiance over a selected wavelength range, wherein the selected wavelength range displays a level of contamination above a selected tolerance level.

In another embodiment, the metrology system 200 may include one or more dynamically adjustable collection field stops configured to modify the spectral radiance of illumination in the collection path 214 in order to mitigate metrology target signal contamination. For example, the dynamically adjustable collection field stop may include, but is not limited to, a detector slit. In a further embodiment, the control system 211 may be communicatively coupled to the dynamically adjustable collection field stop of the collection path 214 of the metrology system 200. In one embodiment, upon receiving one or more characteristics of the one or more metrology targets of the sample 206 from the sensor 210, the control system 211 may selectably adjust the collection field stop of the collection path 214 in order to control signal contamination associated with a given target. In this regard, upon receiving an indication from the sensor 210 that contamination associated with a given metrology target is above a desired tolerance level, the control system 211 may adjust the collection stop of the collection path 214 in order to inhibit transmission highly contaminated portions of the beam reflected from the surface of the sample 206 from reaching the detector 204.

In another embodiment, the control system 211 may be configured to execute a spectral weighting algorithm on detection data in order to mitigate the impact of signal contamination of illumination from one or more metrology targets. In this regard, the spectral weighting algorithm of the control system 211 may be configured to apply more weight to a spectral region of illumination (from the sample 206) in which contamination is below a selected tolerance level. For instance, the spectral weighting algorithm of the control system 211 may be configured to apply more weight to a spectral region of illumination (from the sample 206) in which contamination is negligible or at least minimized.

In another embodiment, the control system 211 may be configured to select the spectral region of the illumination used for analysis of the one or more targets. In this sense, the control system 211 may execute a spectral selection algorithm on detection data in order to select a spectral region of the measured illumination range that displays a level of contamination below a desired level. In turn, the control system 211 may extract one or more metrology parameters associated with the analyzed metrology target using detection data falling within the selected spectral range.

Applicants note that the embodiments described above suitable for carrying out spectral radiance modification of the illumination of the metrology system may be implemented individually or in combination.

Applicants further note that while above description related to spectral radiance modification discusses spectral radiance modification, and spectral detection range selection of detector in combination with the dynamically adjustable illumination pupil, collection pupil, illumination field stop and collection field stop described previously herein, it is recognized that the spectral radiance modification capabilities described above may be implemented in an independent setting. In this regard, the spectral radiance modification capabilities described above may be implemented in a metrology system having fixed illumination and collection pupils and/or fixed illumination and collection field stops.

Figure 3:
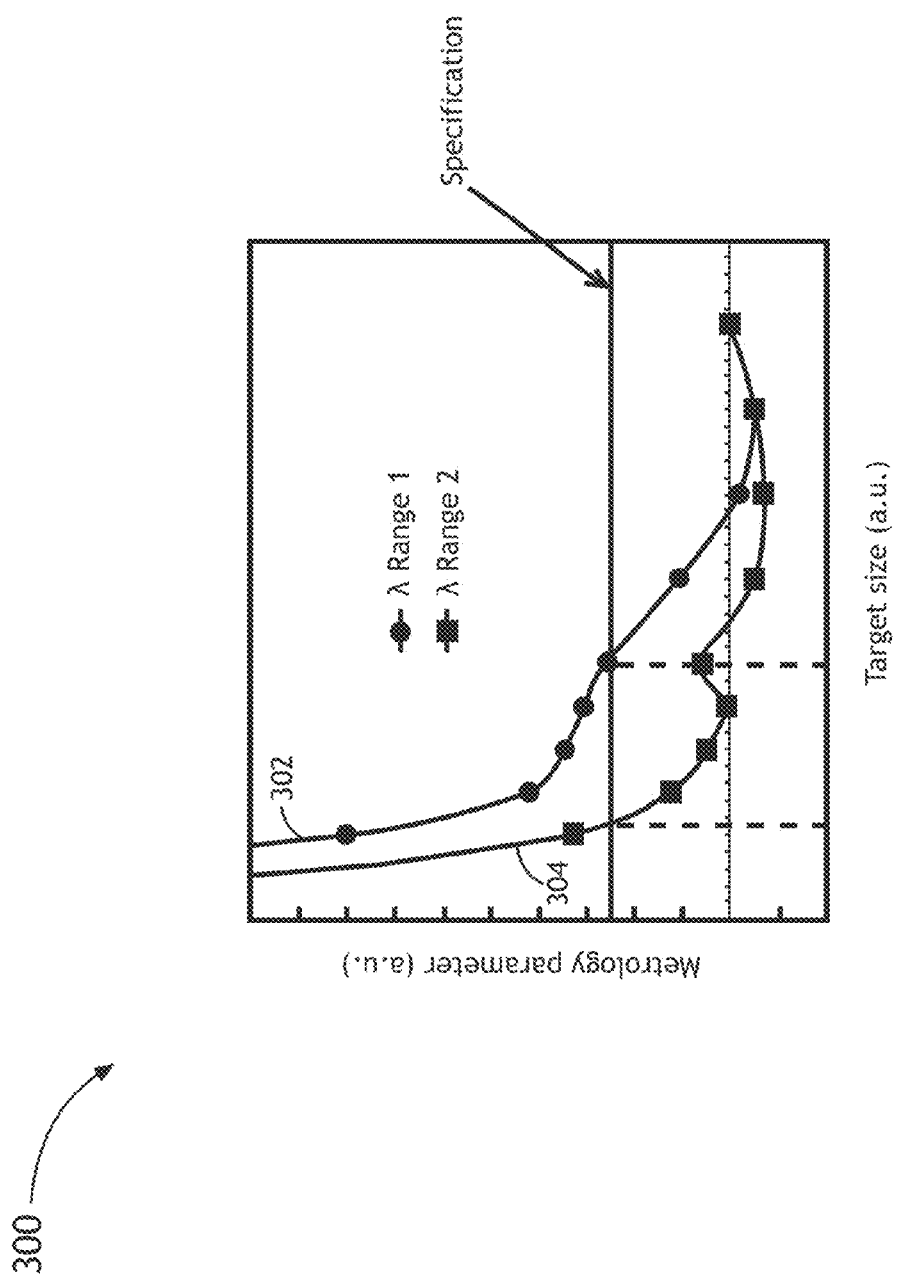
FIG. 3 illustrates metrology tool measurement spot size improvement, in accordance with one embodiment of the present invention.

FIG. 3 illustrates the measurement parameters as a function of target size and wavelength on sample 206. For example, the wavelength selection of illumination source 202 is dynamically adjusted to meet measurement parameter specs at a given target size on sample 206. FIG. 3 illustrates a given metrology parameter as a function of target size for a first wavelength range 302 and a second wavelength range 304. By adjusting the weight given to a given wavelength range, based on the observed level of contamination, the system 200 may mitigate the impact of signal contamination at longer wavelength. In the regard, a wavelength range suitable for meeting the required specification for a given metrology parameter may be determine. In the case illustrated in FIG. 3, the first wavelength range 302 meets the desired specification, wherein the second wavelength range 304 falls below the desired specification. As such, measurement can be carried out using the identified satisfactory wavelength range, namely range 302.

In one embodiment, the control system 211 may consist of a computing system configured to control the dynamically adjustable illumination pupil, the dynamically adjustable collection pupil, the dynamically adjustable illumination field stop, the dynamically adjustable collection field stop in order to enhance the measurement capabilities of the metrology system 200 (discussed in greater detail further herein).

It should be recognized that the various control steps associated with the configuring of the system 200 described throughout the present disclosure may be carried out by a single computer system or, alternatively, a multiple computer system. Moreover, different subsystems of the system 200 may include a computer system suitable for carrying out at least a portion of the steps described above. Further, the one or more computer control systems may be configured to perform any other step(s) of any of the method embodiments described herein.

In another embodiment, the computer control system 211 may be communicatively coupled to the dynamically adjustable illumination pupil 213, the dynamically adjustable collection pupil 215, the dynamically adjustable illumination field stop 216, the dynamically adjustable collection field stop 222, and the various spectral radiance modification means in any manner known in the art. For example, the computer control system 211 may be communicatively coupled to the various subsystems of system 200 via a wireline or wireless connection.

The computer control system 211 may include, but is not limited to, a personal computer system, mainframe computer system, workstation, image computer, parallel processor, or any other device known in the art. In general, the term "computer system," "computing system(s)," or "computer control system" may be broadly defined to encompass any device(s) having one or more processors, which execute instructions from a memory medium.

Program instructions implementing methods such as those described herein may be transmitted over or stored on carrier medium. The carrier medium may be a transmission medium such as a wire, cable, or wireless transmission link. The carrier medium may also include a storage medium such as a read-only memory, a random access memory, a magnetic or optical disk, a magnetic tape, or cloud based storage.

In additional embodiments, the illumination arm 212 and/or the collection arm 214 may include, but are not limited to, one or more additional optical elements, 224 and 226. Those skilled in the art should recognize that numerous optical elements 224/226 may be utilized within the illumination arm 212 or collection arm 214 within the scope of the present invention. For example, the optical elements 224 of the illumination arm 212 may include, but are not limited to, one or more lenses (e.g., focusing lenses), one or more mirrors, one or more filters, or one or more collimators, or one or more fixed apertures, or one or more polarization optics. Similarly, the optical elements 226 of the collection arm 214 may include, but are not limited to, one or more lenses, one or more mirrors, one or more filters, or one or more collimators, or one or more fixed apertures, or one or more polarization optics.

In another aspect of the present invention, the Illumination source 202 may include any broadband illumination source known in the art. In one embodiment, the illumination source 202 may include, but is not limited to, a halogen light source (HLS). For instance, the halogen light source may include, but is not limited to, a tungsten based halogen lamp. In another example, the illumination source 202 may include a xenon arc lamp. By yet another example, the illumination source 202 may include a deuterium arc lamp. By yet another example, the illumination source 102 may include a LED source. In another aspect of the present invention, the Illumination source 102 may include a single illumination source or a plurality of illumination sources. In a general sense, any illumination source capable of producing illumination in the visible, infrared, and ultraviolet spectral ranges is suitable for implementation in the present invention. For example, a xenon arc lamp is capable of delivering light in a spectral range of 10 nm to 2000 nm, with a gradual radiant intensity decrease below 400 nm. In another embodiment, the illumination source 202 may include, but is not limited to, any discharge plasma source known in the art. In yet another embodiment, the illumination source 202 may include, but is not limited to, a laser-driven plasma source.

In another aspect of the present invention, the Illumination source 202 may include any narrow band illumination source known in the art. In one embodiment, the illumination source 202 may include, but is not limited to, one or more laser sources. It should be recognized by those skilled in the art that the above described illumination sources do not represent limitations, but should merely be interpreted as illustrative.

In another aspect of the present invention, the detector 204 may include any light detection system known in the art suitable for implementation in a spectroscopic ellipsometer, spectroscopic unpolarized and polarized reflectometer, or spectroscopic scatterometer setting. In a general sense, any detector capable of measuring spectra across the visible, infrared, and ultraviolet spectral ranges is suitable for implementation in the present invention.

In one embodiment of the present invention, the dynamically adjustable metrology system 200 may dynamically modify one or more illumination characteristics of the metrology system 200 on the measurement plane (e.g., wafer) using an apodizer function to reduce the signal contamination in the metrology system 200. In some embodiments, the illumination characteristics may include, but are not limited to, point spread function (PSF), resolution, contrast, AOI and AZ range and the like. In one embodiment, the apodizer filters may give rise to an optimized or improved spectral intensity spatial distribution, i.e. PSF, with a center lobe (i.e., 0th order) being confined within the spatial extent of metrology target, whereby higher order diffraction peaks at longer wavelength are suppressed (see higher order peaks in FIG. 1B). In one embodiment, the apodizer filter may be positioned at or near illumination pupil stop 216. In an additional embodiment, the shape, size, transmission, phase, and the like of the apodizers filter may be dynamically optimized independent of size and shape of the illumination pupil stop 216 in settings where the apodizer filter is not at the illumination pupil plane. In another embodiment, the illumination field stop 216 may be dynamically varied independently in order to eliminate contribution from the regions of PSF of the illumination most aberrated by the illumination optics 224. In an additional embodiment, one or more sensors 210 inserted in the system 210 may gather information at the illumination field stop 216 and/or the illumination pupil stop 213 and may provide dynamic aperture control in order to adjust the illumination field stop 216 and/or illumination pupil stop 213 to achieve a desired PSF and aberration control at sample plane. In another embodiment, the illumination system response is preferably measured at the sample plane. It is again noted that the illumination pupil 213 and illumination field stop 216 may be dynamically modified independently or simultaneously to form a configuration (e.g., optimum configuration) for achieving desirable PSF (e.g., PSF suitable for providing measurement parameters within an acceptable tolerance level) on the sample plane and suppressing signal contamination.

Figure 4:
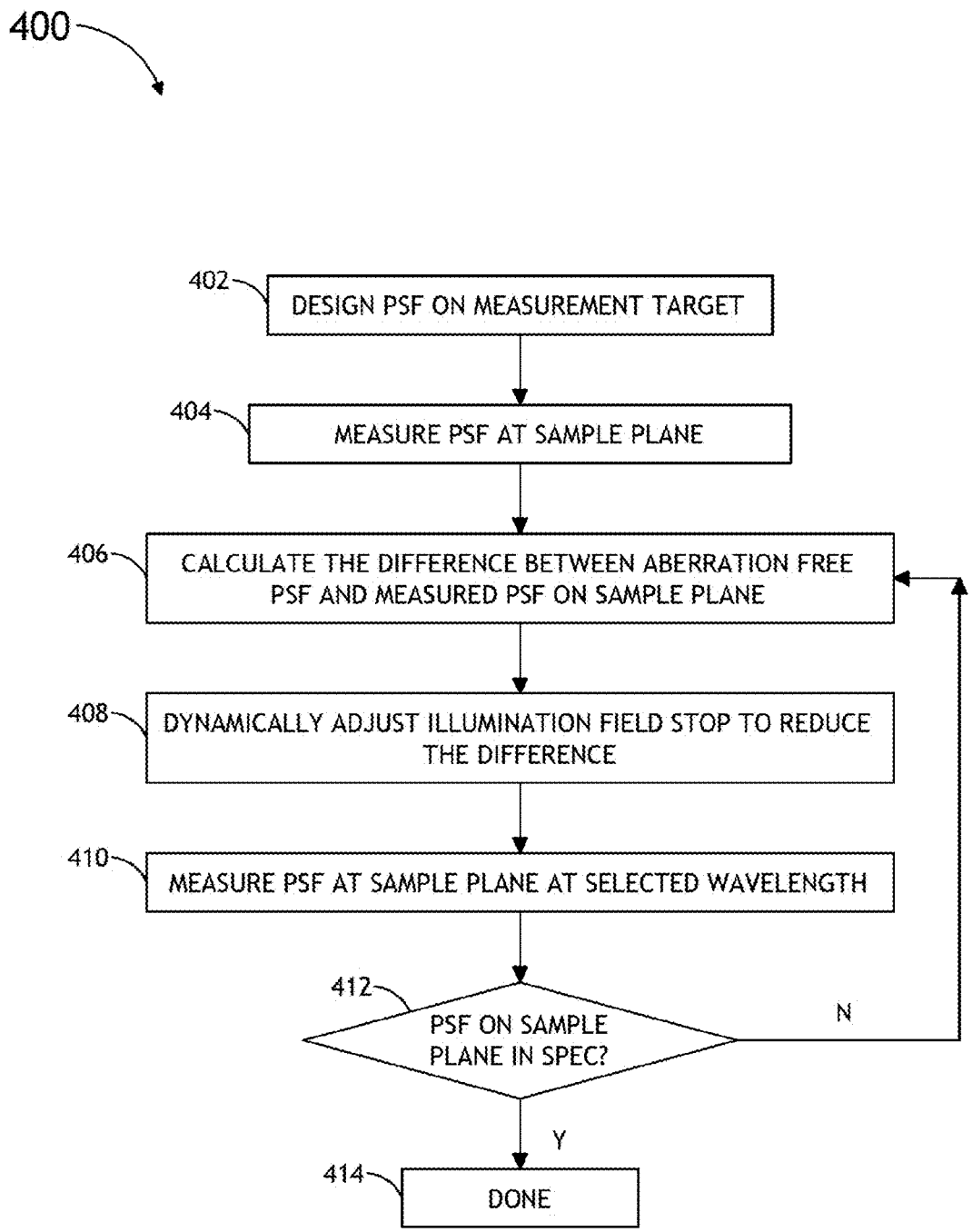
FIG. 4 is a flow diagram illustrating a method for dynamically controlling a metrology system, in accordance with one embodiment of the present invention.

FIG. 4 illustrates a flow diagram for the dynamical adjustment of the metrology system 200, in accordance with one embodiment of the present invention. In step 402, the control system 211 may design a PSF for a measurement target of the sample 206. In this regard, the design of the PSF may be based on the structure and design of the given metrology target of the sample 206. In step 404, the sensor 210 may measure PSF at the sample plane of the sample 206. Then, the sensor 210 may transmit the measurement results to the control system 211. In step 406, the control system 211 may calculate the difference between aberration free PSF and the measured PSF at the sample plane of the sample 206. In step 408, the control system 211 may adjust (e.g., dynamically adjust) the illumination field stop 216 in order to minimize or at least reduce the difference calculated in step 406. Alternatively, the control system 211 may adjust any of the additional adjustable optical components described throughout the present disclosure to minimize the difference of step 406. In step 410, following adjustment, the sensor 210 may again measure PSF at the sample plane of the sample 206. In step 412, the control system 211 may determine whether the measured PSF is within an allowable specification (e.g., selected tolerance level) defined by system software or user input. If the PSF is determined to be out of the desired specification the control system 211 repeats the procedure beginning with step 406. If the PSF is within the desired specification the control system 211 may terminate 414 the adjustment process.

Figure 5:
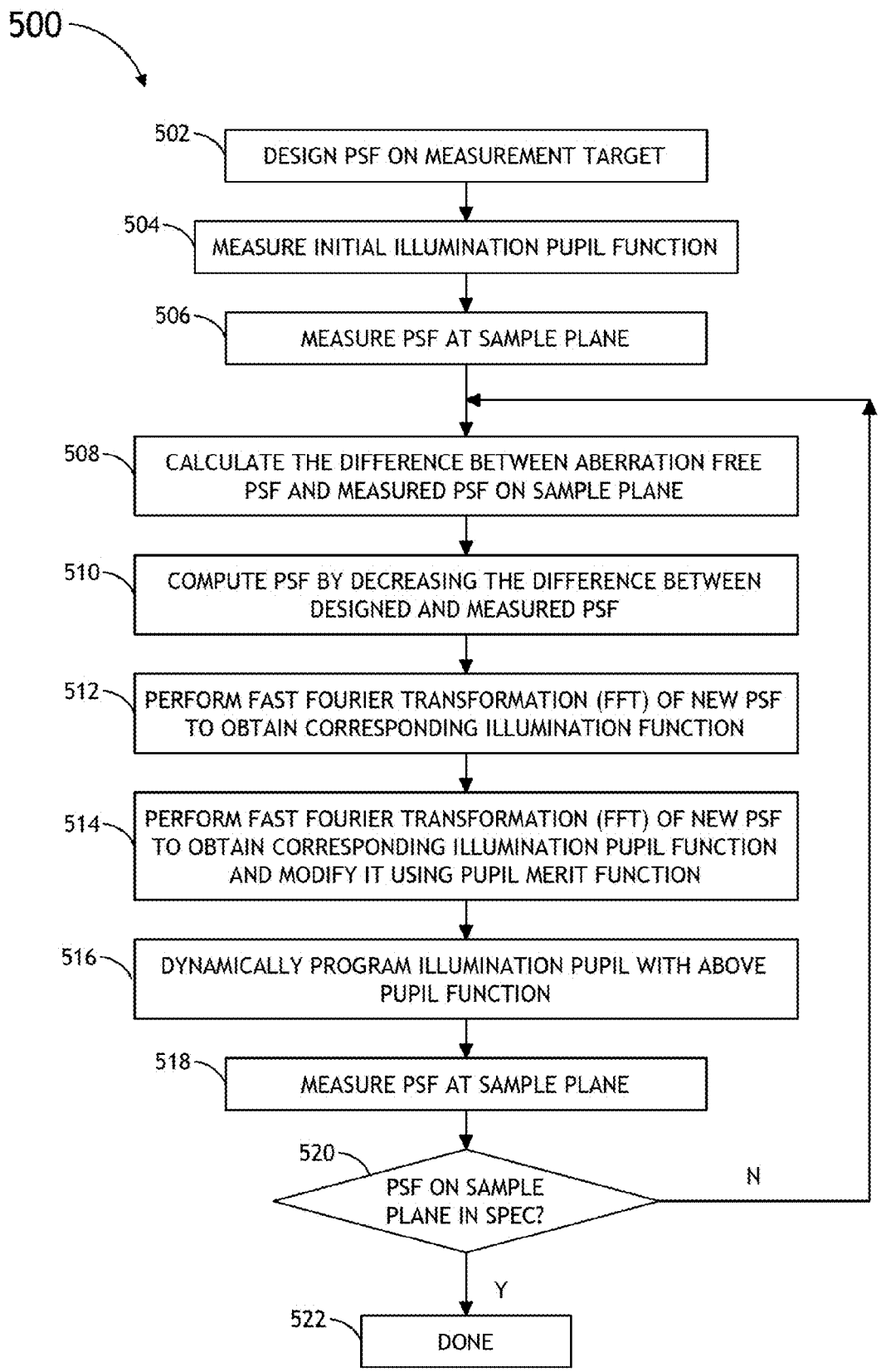
FIG. 5 is a flow diagram illustrating a method for dynamically controlling a metrology system, in accordance with one embodiment of the present invention.

FIG. 5 illustrates a flow diagram for the dynamical adjustment of the metrology system 200, in accordance with another embodiment of the present invention. In step 502, the control system 211 may design a PSF for a measurement target of the sample 206. In this regard, the design of the PSF may be based on the structure and design of the given metrology target of the sample 206. In step 504, the sensor 210 may measure the initial illumination pupil function associated with the illumination pupil 213. In step 506, the sensor 210 may measure the PSF at the sample plane of the sample 206. Then, the sensor 210 may transmit the measurement results to the control system 211. In step 508, the control system 211 may calculate the difference between aberration free PSF and the measured PSF at the sample plane of the sample 206. In step 510, the control system 211 may compute a new PSF by decreasing the difference between the designed PSF and the measured PSF. In step 512, the control system 211 may perform a fast Fourier transformation (FFT) on the new PSF in order to obtain the corresponding illumination function of the new PSF. In step 514, the control system 211 may perform a fast Fourier transformation (FFT) on the new PSF in order to obtain the corresponding illumination function of the new PSF and modify the new pupil function using a pupil merit function. In step 516, the control system 211 may dynamically program the illumination pupil 213 with the pupil function found in steps 512/514. In step 518, the sensor 210 may again measure PSF at the sample plane of the sample 206. In step 520, the control system 211 may determine whether the measured PSF is within an allowable specification (e.g., selected tolerance level) defined by system software or user input. If the PSF is determined to be out of the desired specification the control system 211 repeats the procedure beginning with step 508. If the PSF is within the desired specification the control system 211 may terminate 522 the adjustment process.

In another embodiment of the present invention, the metrology system 200 may control and mitigate diffraction induced signal contamination by controlling signal contamination caused by target edge diffraction (see FIG. 1C) utilizing an adjustable collection pupil aperture/apodizer. Applicants note that the projection of signal contamination from outside a designated measurement target onto the collection pupil varies significantly as a function of target size and illumination wavelength. In one embodiment, variable shape aperture control includes changing collection aperture geometric shape and size, programming transmission function and phase as a function of pupil coordinates. For example, a MEMS optical element may be configured as apodizer filter in one-dimension (e.g., AOI direction) or two-dimension (e.g., AOI direction and AZ direction) with desired azimuth angle range. In some embodiments, the system 200 may include mechanically selectable collection pupil apertures/apodizers having selected designs. In other embodiments, the system 200 may include tunable transmission or reflection MEMS inserted into collection pupil plane of the system 200. The selection of shape or apodization pattern may be determined either by modeling software executed by the control system 211 or by differential measurement of the optical response to changes in collection pupil pattern.

In combination of the illumination side source slit and beam shaping by apodizer filter, signal contamination is further improved by using different field stop shape, such as slit B instead of rectangular slit A (see FIG. 6). Thus by inference, the measurement spot size of oblique spectral Ellipsometer/scatterometer would be reduced further than just using optimized illumination field stop and illumination pupil.

Figure 6A:
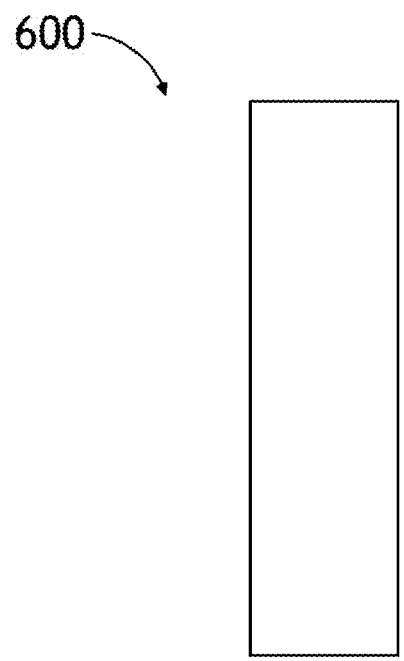
FIG. 6A illustrates a rectangular detector slit, in accordance with one embodiment of the present invention.
Figure 6B:
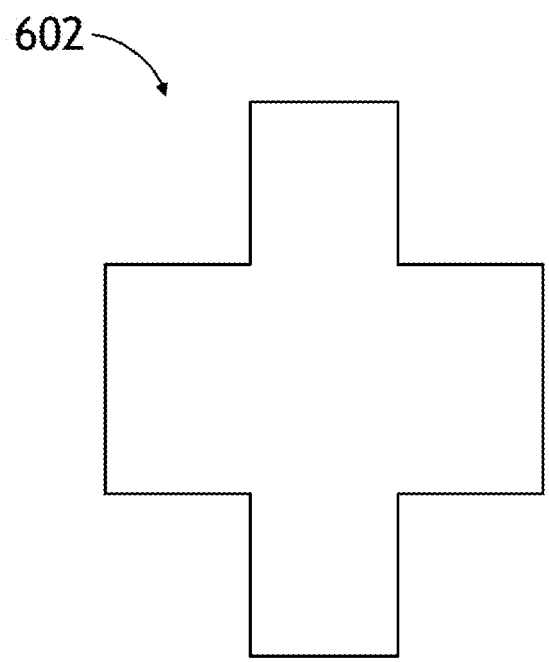
FIG. 6B illustrates a cross-shaped detector slit, in accordance with one embodiment of the present invention.
Figure 6D:
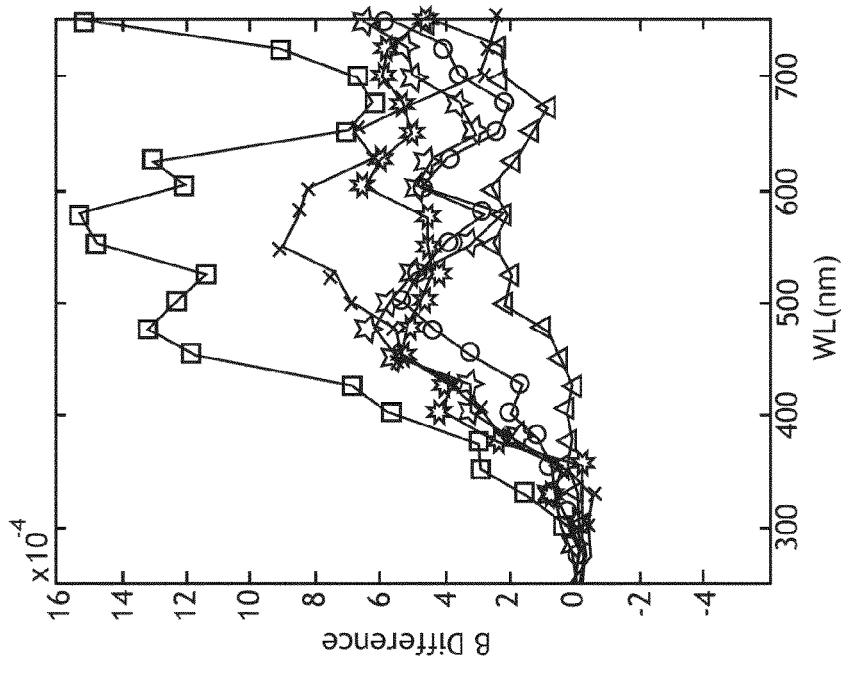
FIG. 6D illustrates a simulated signal contamination using a cross-shaped detector slit, in accordance with one embodiment of the present invention.
Figure 6C:
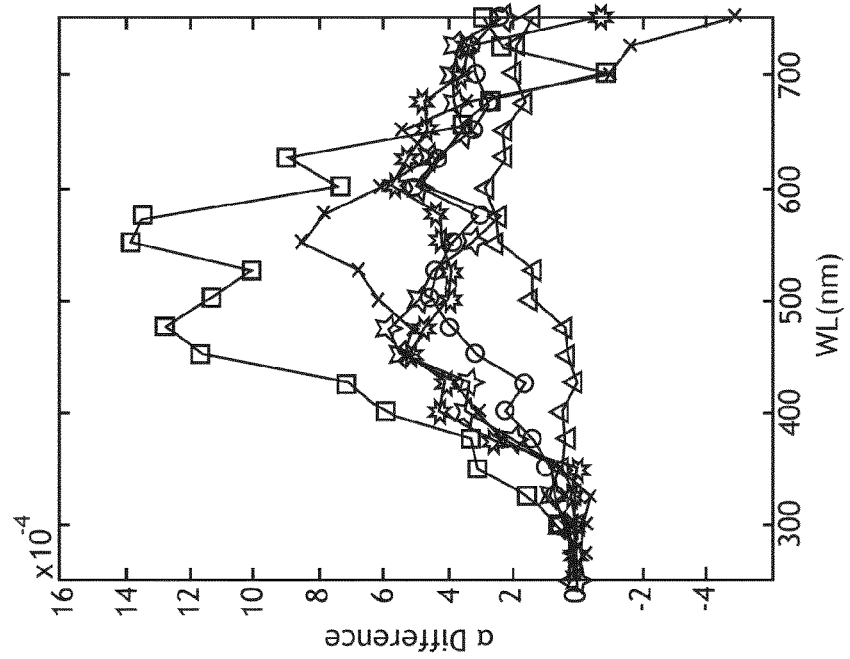
FIG. 6C illustrates a simulated signal contamination using a rectangular detector slit, in accordance with one embodiment of the present invention

FIGS. 6A-6B illustrate examples of slit geometries of the dynamically adjustable illumination and collection field stop. In some embodiments, the slit shape may include, but is not limited to, a circle, a rectangle, an ellipse, or an irregular shape. FIG. 6A depicts a rectangular slit 600, while FIG. 6B depicts a cross-shaped slit 602. FIGS. 6C-6D illustrate simulated signal contamination for slit 600 and slit 602 respectively. The data illustrated in FIGS. 6C-6D depicts a generally increasing variance in the difference in a parameter as a function of wavelength as the size of the measured metrology target shrinks. Applicants note that curves illustrated in FIGS. 6C-6D correspond to target sizes of 30, 35, 40, 45, 50, and 55 μm, with the smallest target of 30 μm displaying the largest parameter difference variance and the largest target (55 μm) displaying the most constant parameter difference as a function of wavelength. In this regard, a slit shape that meets the desired signal contamination specification may be selected and implemented.

Figure 7:
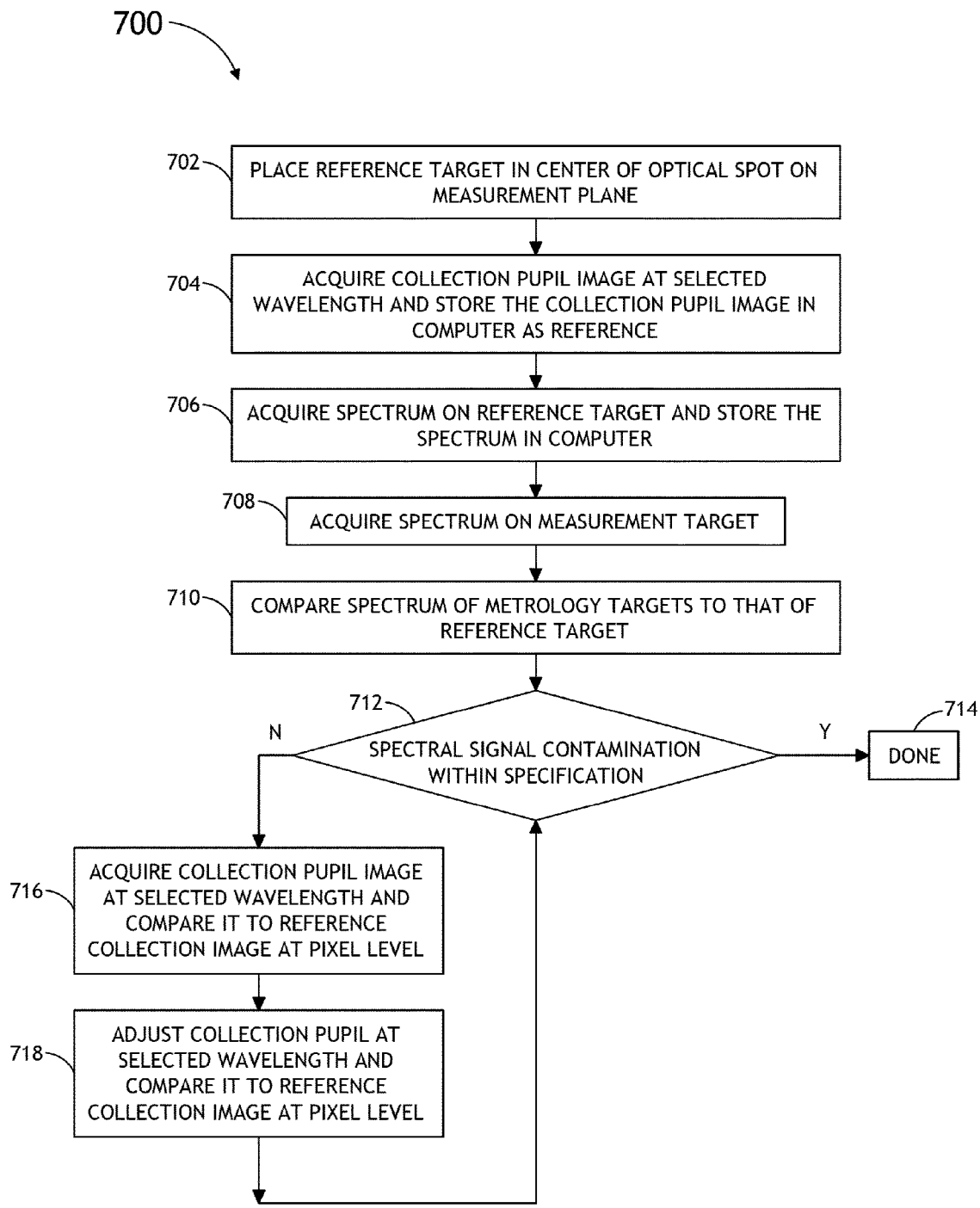
FIG. 7 is a flow diagram illustrating a method for dynamically controlling a metrology system, in accordance with one embodiment of the present invention.

FIG. 7 illustrates a flow diagram for the dynamical adjustment of the metrology system 200, in accordance with another embodiment of the present invention. In step 702, a reference target may be placed in the center of the optical spot of the measurement plane of the sample 206. In step 704, the sensor 210 may acquire a collection pupil image at a selected wavelength from the collection pupil 215. The control system 211 may then store the collection pupil image in computer memory as reference. In step 706, the sensor 210 may acquire spectrum data from the reference target. The control system 211 may then store the spectrum data in computer memory as reference. In step 708, the sensor 210 may acquire spectrum data from a measurement target on the sample 206. Then, the sensor 210 may transmit the spectrum data from the measurement target to the control system 211. In step 710, the control system 211 may compare the spectrum data of the one or more measured metrology targets to that of the stored spectrum data of the reference metrology target. In step 712, the control system 211 may determine whether the spectral signal contamination is within an allowable specification (e.g., selected tolerance level) defined by system software or user input. If the signal contamination is within the desired specification the control system 211 may terminate 714 the adjustment process. If the signal contamination is determined to be out of the desired specification the control system 211 repeats the procedure continues with step 716. In step 716, the sensor 210 may acquire an additional collection pupil image at a selected wavelength. Then, the control system 211 may compare the collection pupil image to the stored reference collection pupil image on a pixel level basis. In step 718, the control system 211 may adjust the collection pupil at the selected wavelength. Then, the control system 211 may again compare the collection pupil image to the stored reference collection pupil image on a pixel level basis. Then, the control system 211 may again determine whether determine whether the spectral signal contamination is within an allowable specification and either repeat steps 714-718 until a desired specification level is attained or terminate the process at step 714.

Figure 8:
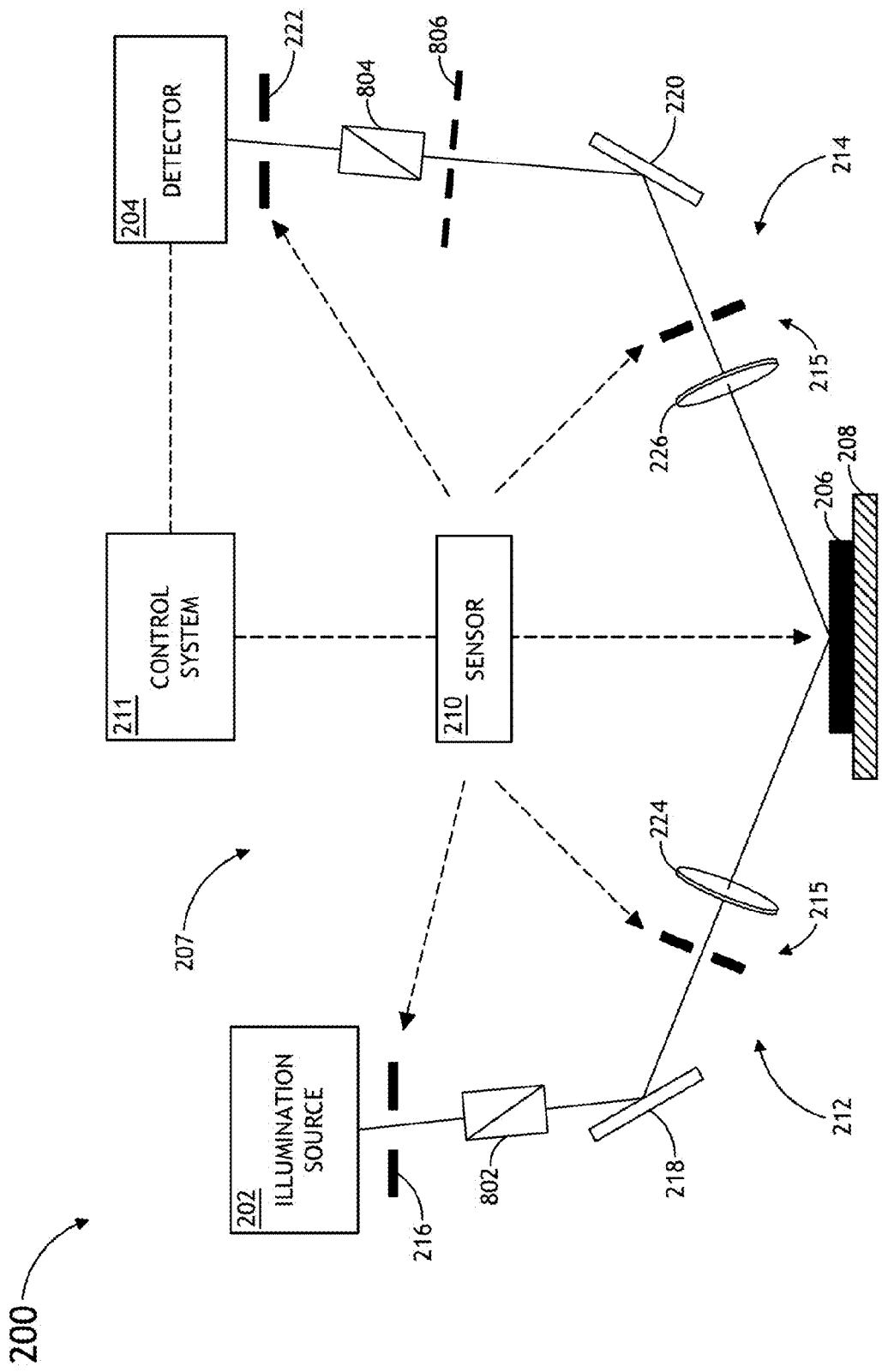
FIG. 8 illustrates a block diagram view of a dynamically adjustable metrology system, in accordance with an alternative embodiment of the present invention.

In an alternative embodiment, illustrated in FIG. 8, the dynamically adjustable metrology system 200 may be equipped with multiple polarizing elements. In this regard, the system 200 may be configured to as a spectroscopic ellipsometer. In one aspect, the system 200 may include one or more first polarizing elements 802 positioned in the illumination arm 212. For example, the one or more first polarizing elements 802 may be positioned between the illumination field stop 216 and the illumination pupil 215. In another aspect, the system 200 may include one or more second polarizing elements positioned in the illumination arm 212. For example, the first polarizing element may be positioned between the illumination field stop 216 and the illumination pupil 215. In one embodiment, the one or more first polarizing elements may include, but are not limited to, at least one of a polarizer and a compensator. In another embodiment, the one or more second polarizing elements may include, but are not limited to, at least one of an analyzer and a compensator. In a further embodiment, the metrology system 200 may include a waveplate 806.

Figure 9B:
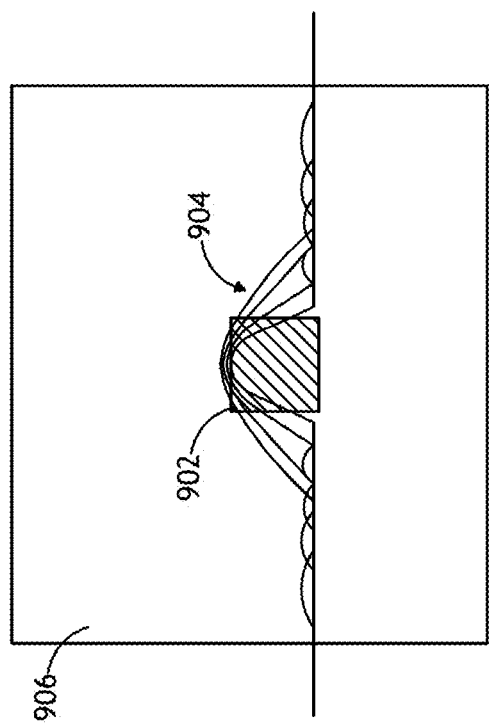
FIGS. 9A-9B illustrate a simplified schematic view of a metrology target surrounded by a highly absorbing material, in accordance with an embodiment of the present invention.
Figure 9A:
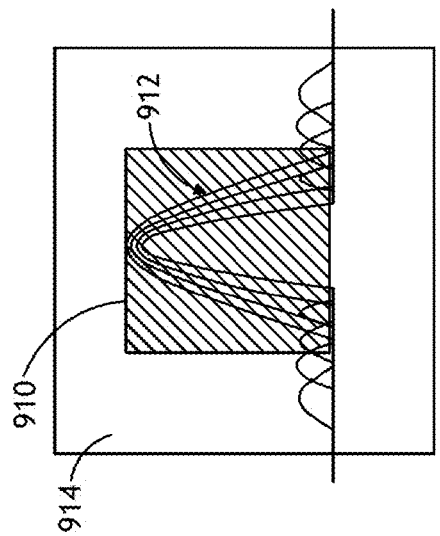

FIGS. 9A-9B illustrate an engineered target surrounded by an illumination absorbing material, in accordance with one embodiment of the present invention. It is noted herein that for metrology targets having a size smaller than the central lobe diffraction lobe (0th order), as shown in FIG. 9A, the signal contamination may exist over the entire spectral range of the metrology system. In this setting, the adjustment of the spectral region, illumination pupil stop, collection pupil stop, illumination field stop and collection field stop, as described previously herein, may no longer be capable of mitigating the problem. In this case, the target may be surrounded by light absorbing material 906, 914 disposed within the vicinity of the one or more metrology targets 902, 910, as shown by the larger square outside the target (see FIGS. 9A and 9B). In this regard, the surrounding material may be disposed about the give target so as to absorb all the PSF lobes for all wavelengths falling outside the measure target. One such material includes a carbon-nanotube coating deposited on Si. Such a coating may be capable of absorbing approximately 99 percent of the ultraviolet, visible, infrared and far-infrared light that strikes it. In yet another embodiment, other coating materials having high NIR or VIS wavelength absorption may be deposited outside the target in such a way that it only absorbs the wavelength having PSF lobe falling outside the target (see FIG. 9B). In the case shown in FIG. 9B, the light absorbing material approach may be combined with any of the embodiments described previously herein.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A dynamically adjustable metrology system, comprising:
    an illumination source configured to illuminate one or more metrology targets disposed on a surface of a sample disposed on a sample stage;
    a spectrograph configured to measure spectral properties of at least a portion of light reflected from the one or more metrology targets;
    a selectably adjustable optical system including an illumination arm and a collection arm, the illumination source and the detector being optically coupled by the optical system, the optical system further including at least one of the group including:
        a dynamically adjustable illumination pupil positioned in the illumination arm;
        a first polarizing element positioned in the illumination arm;
        a dynamically adjustable illumination field stop positioned in the illumination arm;
        a dynamically adjustable collection pupil positioned in the collection arm;
        a second polarizing element disposed in the collection arm; and
        a dynamically adjustable collection field stop positioned in the collection arm;
    a sensor configured to measure one or more optical characterics of at least one of the dynamically adjustable illumination pupil, the dynamically adjustable collection pupil, the dynamically adjustable illumination field stop the dynamically adjustable collection field stop and one or more metrology targets of the sample; and
    a control system communicatively coupled to the dynamically adjustable illumination pupil, the dynamically adjustable collection pupil, the dynamically adjustable illumination field stop and the dynamically adjustable collection field stop, wherein the control system is configured to:
        receive one or more optical characteristics of at least one of the dynamically adjustable illumination pupil, the dynamically adjustable collection pupil, the dynamically adjustable illumination field stop and the dynamically adjustable collection field stop from the sensor;
        monitor one or more optical characteristics at one or more metrology targets of the sample; and
        responsive to the measured one or more optical characteristics, selectably dynamically adjust at least one of the illumination pupil, the collection pupil, the illumination field stop, the collection field stop, and a spectral radiance of the illumination source.

2. The apparatus of claim 1, wherein the control system is configured to selectably adjust at least one of the illumination pupil and the collection pupil in order to control at least one of a numerical aperture (NA), an angle of incidence (AOI), an azimuth angle (AZ) and pupil apodization of the metrology system.

3. The apparatus of claim 1, wherein the control system is configured to selectably adjust the illumination field stop and the collection field stop in order to control a field of view (FOV) of the metrology system.

4. The apparatus of claim 1, wherein the control system is configured to selectably adjust the spectral radiance of the illumination source in order to reduce signal contamination below a selected tolerance level.

5. The apparatus of claim 4, wherein the illumination source comprises:
    a dynamically adjustable illumination source, wherein one or more spectral characteristics of the illumination source are adjustable in response to the control system.

6. The apparatus of claim 4, further comprising:
    a dynamically adjustable filter configured to attenuate spectral radiance at a wavelength range having a contamination level above a selected tolerance level.

7. The apparatus of claim 4, wherein the control system is configured to selectably adjust a spectral radiance of illumination from the sample utilizing a spectral radiance weighting algorithm.

8. The apparatus of claim 4, wherein the control system is further configured to:
    selectably adjust at least one of the illumination pupil, the collection pupil, the illumination field stop, the collection field stop, and the spectral radiance in order to inhibit contamination associated with one or more metrology targets below a selected contamination level.

9. The apparatus of claim 4, wherein the control system is further configured to:
    selectably adjust at least one of the illumination pupil, the collection pupil, the illumination field stop, the collection field stop, and the spectral radiance in order to adjust the point spread function ("PSF") of illumination at a sample plane of the sample.

10. The apparatus of claim 9, wherein the control system is configured to selectably adjust at least one of the illumination pupil, the collection pupil, the illumination field stop, the collection field stop, and the spectral radiance in order to optimize the PSF of illumination at a sample plane of the sample.

11. The apparatus of claim 1, wherein the control system is further configured to:
selectably adjust a spectral radiance of the illumination source in order to optimize metrology measurement capabilities for each metrology target of the sample.

12. The apparatus of claim 1, wherein the dynamically adjustable illumination pupil of the illumination arm comprises:
at least one of a one-dimensional and two-dimensional reflective micro electro-mechanical systems ("MEMS") mirror situated at or near the illumination pupil configured to dynamically adjust at least one of an angle of incidence ("AOI"), an azimuthal angle ("AZ"), a numerical aperture ("NA"), and pupil apodization of the illumination from the illumination source.

13. The apparatus of claim 1, wherein the dynamically adjustable collection pupil of the collection arm comprises:
at least one of one-dimension and two-dimensional reflective micro electro-mechanical systems ("MEMS") mirror situated at or near the collection pupil configured to dynamically adjust at least one of an angle of incidence ("AOI"), an azimuthal angle ("AZ"), a numerical aperture ("NA"), and pupil apodization of the illumination from the one or more metrology targets.

14. The apparatus of claim 1, wherein the dynamically adjustable illumination pupil of the illumination arm comprises:
at least one of one-dimensional and two-dimensional liquid crystal cell spatial light modulator situated at or near the illumination pupil configured to dynamically adjust at least one of an angle of incidence ("AOI"), an azimuthal angle ("AZ"), a numerical aperture ("NA"), and pupil apodization of the illumination from the illumination source.

15. The apparatus of claim 1, wherein the dynamically adjustable collection pupil of the collection arm comprises:
a two-dimensional liquid crystal cell spatial light modulator situated at or near the collection pupil configured to dynamically adjust at least one of an angle of incidence ("AOI"), an azimuthal angle ("AZ"), a numerical aperture ("NA"), and pupil apodization of the illumination from the one or more metrology targets.

16. The apparatus of claim 1, wherein the dynamically adjustable collection field stop of the collection arm comprises:
a one dimensional or two-dimensional liquid crystal cell spatial light modulator configured to dynamically adjust a field of view (FOV) of the metrology system.

17. The apparatus of claim 1, wherein the dynamically adjustable illumination field stop of the illumination arm comprises:
a one dimensional or two-dimensional liquid crystal cell spatial light modulator configured to dynamically adjust a field of view (FOV) of the metrology system.

18. The apparatus of claim 1, wherein the dynamically adjustable collection field stop of the collection arm comprises:
a micro electro-mechanical systems ("MEMS") device configured to dynamically adjust a field of view (FOV) of the metrology system.

19. The apparatus of claim 1, wherein the dynamically adjustable illumination field stop of the illumination arm comprises:

a micro electro-mechanical systems ("MEMS") device configured to dynamically adjust a field of view (FOV) of the metrology system.

20. The apparatus of claim 1, wherein the sensor is configured to measure an illumination point spread function at a sample plane of the sample.

21. The apparatus of claim 1, wherein the sensor is configured to measure an illumination spot size at a sample plane of the sample.

22. The apparatus of claim 1, wherein the sensor is configured to measure one or more scattering characteristics at a sample plane of the sample.

23. The apparatus of claim 1, wherein the sensor is configured to measure one or more wavefront characteristics at a sample plane of the sample.

24. The apparatus of claim 1, wherein the sensor is configured to measure at least one of angle of incidence, azimuthal angle, field of view, and numerical aperture of illumination at the sample plane of the sample.

25. The apparatus of claim 1, wherein the optical characteristics monitored by the control system comprise:
at least one of a point spread function ("PSF") of illumination at a sample plane of the sample, a spot size of illumination at a sample plane of the sample, and one or more scattering characteristics at a sample plane of the sample.

26. The apparatus of claim 1, wherein the illumination source comprises:
at least one broad band illumination source.

27. The apparatus of claim 1, wherein the illumination source comprises:
at least one narrow band light source.

28. The apparatus of claim 1, wherein the control system is further configured to:
selectably adjust a spectral radiance of the illumination source in order to reduce signal contamination below a selected tolerance level.

29. The apparatus of claim 1, wherein the dynamically adjustable illumination pupil of the illumination arm comprises:
a two-dimensional reflective micro electro-mechanical systems ("MEMS") mirror situated at or near the illumination pupil configured to dynamically adjust illumination at least one of an angle of incidence ("AOI"), an azimuthal angle ("AZ"), a numerical aperture ("NA"), and apodization of the illumination from the illumination source.

30. The apparatus of claim 1, wherein the dynamically adjustable collection pupil of the collection arm comprises:
A two-dimensional reflective micro electro-mechanical systems ("MEMS") mirror situated at or near the collection pupil configured to dynamically adjust at least one of an angle of incidence ("AOI"), an azimuthal angle ("AZ"), a numerical aperture ("NA"), and apodization of the illumination from the one or more metrology targets.

31. The apparatus of claim 1, wherein the dynamically adjustable illumination pupil of the illumination arm comprises:
a two-dimensional liquid crystal cell spatial light modulator situated at or near the illumination pupil configured to dynamically adjust illumination at least one of an angle of incidence ("AOI"), an azimuthal angle ("AZ"), a numerical aperture ("NA"), and apodization of the illumination from the illumination source.

32. The apparatus of claim 1, wherein the dynamically adjustable collection pupil of the collection arm comprises:

a two-dimensional liquid crystal cell spatial light modulator situated at or near the collection pupil configured to dynamically adjust at least one of an angle of incidence ("AOI"), an azimuthal angle ("AZ"), a numerical aperture ("NA"), and apodization of the illumination from the one or more metrology targets.

33. The apparatus of claim 1, wherein the dynamically adjustable collection field stop of the collection arm comprises:
   a two-dimensional liquid crystal cell spatial light modulator configured to dynamically adjust a field of view (FOV) of the metrology system.

34. The apparatus of claim 1, wherein the dynamically adjustable illumination field stop of the illumination arm comprises:
   a two-dimensional liquid crystal cell spatial light modulator configured to dynamically adjust a field of view (FOV) of the metrology system.

35. The apparatus of claim 1, wherein the dynamically adjustable collection field stop of the collection arm comprises:
   a EMS micro electro-mechanical systems ("MEMS") configured to dynamically adjust a field of view (FOV) of the metrology system.

36. The apparatus of claim 1, wherein the dynamically adjustable illumination field stop of the illumination arm comprises:
   a micro electro-mechanical systems ("MEMS") device configured to dynamically adjust a field of view (FOV) of the metrology system.

37. The apparatus of claim 1, wherein the illumination source comprises:
   at least one broad band illumination source.

38. The apparatus of claim 1, wherein the illumination source comprises:
   at least one narrow band light source.

39. The apparatus of claim 1, wherein the first polarizing element comprises:
   at least one of a polarizer and compensator.

40. The apparatus of claim 1, wherein the second polarizing element comprises:
   at least one of a compensator and analyzer.

41. The apparatus of claim 1, further comprising:
   an layer of illumination absorbing material disposed about the one or more metrology targets, wherein the illumination absorbing material is suitable for absorbing at least 95% of illumination impinging on the illumination absorbing material.

* * * * *